(12) United States Patent
Henderson et al.

(10) Patent No.: US 11,426,363 B2
(45) Date of Patent: Aug. 30, 2022

(54) COMPOSITIONS INCLUDING CANNABIS AND AVOCADO/SOYBEAN UNSAPONIFIABLES AND METHODS OF USE

(71) Applicant: Nutramax Laboratories, Inc., Lancaster, SC (US)

(72) Inventors: Todd R. Henderson, Lancaster, SC (US); David Griffin, Forest Hill, MD (US)

(73) Assignee: NUTRAMAX LABORATORIES, INC., Lancaster, SC (US)

( * ) Notice: Subject to any disclaimer, the term of this patent is extended or adjusted under 35 U.S.C. 154(b) by 253 days.

(21) Appl. No.: 16/930,513

(22) Filed: Jul. 16, 2020

(65) Prior Publication Data

US 2021/0023022 A1 Jan. 28, 2021

Related U.S. Application Data

(60) Provisional application No. 62/879,209, filed on Jul. 26, 2019.

(51) Int. Cl.
*A61K 31/05* (2006.01)
*A61P 29/00* (2006.01)
*A61K 36/48* (2006.01)
*A61K 36/54* (2006.01)
*A61K 9/00* (2006.01)

(52) U.S. Cl.
CPC .............. *A61K 31/05* (2013.01); *A61K 36/48* (2013.01); *A61K 36/54* (2013.01); *A61P 29/00* (2018.01); *A61K 9/0053* (2013.01)

(58) Field of Classification Search
None
See application file for complete search history.

(56) References Cited

U.S. PATENT DOCUMENTS

2017/0239349 A1* 8/2017 Agadjanyan ........... A61K 39/39

OTHER PUBLICATIONS

Grazio, et al., Acta Clin Croat, 50:513. (Year: 2011).*
Martel-Pelletier, et al., Bone, 51:297. (Year: 2012).*
Gamble, L. J., et al. "Pharmacokinetics, Safety, and Clinical Efficacy of Cannabidiol Treatment in Osteoarthritic Dogs", Front Vet Sci, 5: 165 Jul. 23, 2018.

Agurell, S., et al. "Interactions of delta 1-tetrahydrocannabinol with cannabinol and cannabidiol following oral administration in man. Assay of cannabinol and cannabidiol by mass fragmentography", Experientia, 37(10): 1090-1092 (1981).
Guy, G.W., et al. "A Phase I, Open Label, Four-Way Crossover Study to Compare the Pharmacokinetic Profiles of a Single Dose of 20 mg of a Cannabis Based Medicine Extract (CBME) Administered on 3 Different Areas of the Buccal Mucosa and to Investigate the Pharmacokinetics of CBME per Oral in Healthy Male and Female Volunteers", Journal of Cannabis Therapeutics, 3(4): 79-120) 2004.
Nadulski, T., et al. "Simultaneous and sensitive analysis of THC, 11-OH-THC, THC-COOH, CBD, and CBN by GC-MS in plasma after oral application of small doses of THC and cannabis extract", J Anal Toxicol, 29(8): 782-9, Nov. 2005.
Taylor, L., et al., "A Phase I, Randomized, Double-Blind, Placebo-Controlled, Single Ascending Dose, Multiple Dose, and Food Effect Trial of the Safety, Tolerability and Pharmacokinetics of Highly Purified Cannabidiol in Healthy Subjects", CNS Drugs, 32(11): 1053-1067) 2018.
Trevoux, R., "Unsaponifiable fractions of the avocado and soybean in gynecology," J. Gynecol. Obstet. Biol. Reprod. 6 (1): 99-105 (Jan. 1977) (Abstract).
Lamaud, M.E., et al., "Biochemical modifications of connective tissue induced by the non-saponifiables of avocado and soy-bean oils administered percutaneously in the hairless rat," Pathol. Biol. 26 (5): 269-74 (May-Jun. 1978). (Abstract).
Boumediene, K., et al., "Avocado/soya unsaponifiables enhance the expression of transforming growth factor beta 1 and beta 2 in cultured articular chondrocytes," Arthritis Rheum. 42 (1): 148-56 (Jan. 1999).
Henrotin, Y.E., et al., "Effects of three avocado/soybean unsaponifiable mixtures on metalloproteinases, cytokines and prostaglandin E2 production by human articular chondrocytes," Clin. Rheumatol. 17 (1): 31-9 (1998).
Maheu, E. et al. "Symptomatic efficacy of avocado/soybean unsaponifiables in the treatment of osteoarthritis," Arthritis Rheum. 41 (1): 81-91 (Jan. 1998).
Blotman, F., et al., "Efficacy and safety of avocado/soybean unsaponifiables in the treatment of symptomatic osteoarthritis," Rev. Rheum. Engl. Ed. 64 (12): 825-34 (Dec. 1997).
Thiers, M.H. "Unsaponifiable constituents of avocado and soya oils. Treatment of certain forms of arthralgia," Journal de Medecine de Lyon 53 (222): 195-8 (1972).

* cited by examiner

*Primary Examiner* — Michael Barker
(74) *Attorney, Agent, or Firm* — Dickinson Wright PLLC; Andrew D. Dorisio

(57) ABSTRACT

The present application relates to compositions comprising avocado/soybean unsaponifiables ("ASU") and *cannabis*, and related methods of use. In one embodiment, the *cannabis* is a *cannabis* oil extract that is combined with ASU to reduce inflammatory responses and inflammation in humans and animals.

23 Claims, 6 Drawing Sheets

COMPOSITIONS INCLUDING CANNABIS AND AVOCADO/SOYBEAN UNSAPONIFIABLES AND METHODS OF USE

This application claims priority to U.S. Provisional Patent Application Ser. No. 62/879,209 filed on Jul. 26, 2019, the entirety of the contents of which is incorporated by reference herein.

TECHNICAL FIELD

The present disclosure relates to compositions for promoting connective tissue health. In particular, the disclosure relates to compositions comprising combinations of *cannabis* and avocado/soybean unsaponifiables (ASU) that exhibit synergistic properties.

BACKGROUND

Connective tissue is the structural framework of cartilage, bone, synovium, ligament, meniscus, and tendon in articulating joints. Components of connective tissue are produced by resident cells and then secreted to form the extracellular matrix ("ECM") characteristics of the tissue. In addition to serving as structural framework, the ECM also plays a critical role in cell communication and function. In articular cartilage, chondrocytes are aligned in a distinct pattern within the type II collagen ECM framework. Bone forming osteoblasts and osteocytes, as well as bone resorbing osteoclasts, are organized in mineralized type I collagen ECM. The few fibroblast-like and macrophage-like cells in the synovium are also held in place by ECM. Similarly, tenocytes and ligament cells are assembled together within the ECM. The synthesis and breakdown of connective tissue ECM is controlled by a network of regulatory molecules which are also produced by the resident tissue cells. This network includes growth factors and a wide array of molecules known as pro-inflammatory mediators, which include cytokines, prostaglandins and nitric oxide. These molecules exhibit many biological activities. They can induce cell proliferation or cell death and can also induce anabolic pathways for production of ECM or catabolic enzymes that can break down the ECM. The production and function of regulatory molecules is modulated by many factors including mechanical forces, physical factors, such as, temperature and pH, chemicals, microbes and their products. Under certain conditions, these factors can elicit excessive and untimely production of regulatory molecules leading to irreparable tissue damage, loss of function and death.

Biological tissues may react to mechanical, physical, chemical insults and infection with an inflammatory response, a kind of biological defense reaction, that may be accompanied by symptoms including, among other things, flare, swelling, pyrexia, and pain. The inflammation process is known to lead to recovery, to healing, defense against infection and is usually life preserving. The inflammatory response in humans and animals consists of two phases. The initial phase is characterized by the local synthesis of pro-inflammatory mediators such prostaglandins and leukotrienes, which are derived from arachidonic acid through the action of cyclooxygenases and lipoxygenases. These pro-inflammatory mediators increase local blood flow and enhance the permeability of endothelial cells to allow leukocyte recruitment and accumulation. Other pro-inflammatory mediators that are subsequently produced include nitric oxide and cytokines (including, but not limited to, interleukin-1β ("IL-1β"), interleukin-6 ("IL-6"), chemokines such as interleukin-8 ("IL-8"), and tumor necrosis factors ("TNFs") including TNF-α). In the second phase, the resolution phase, prostaglandins generated during the initial phase activate enzymatic pathways along which arachidonic acid is converted to chemical mediators with anti-inflammatory properties. It has been reported that prostaglandin $E_2$ ("$PGE_2$") activates the expression of 15-lipoxygenase which generates anti-inflammatory lipoxins from arachidonic acid. Thus, the resolution of inflammation is driven by the pro-inflammatory response. Studies indicate that the initiation, progression and termination of the inflammation process are tightly controlled. Prolonged, exaggerated inflammation has been associated with many disorders including osteoarthritis, rheumatoid arthritis, Alzheimer's disease and cardiovascular disease.

In joint tissues, chondrocytes, synoviocytes, osteoblasts, osteoclasts, ligament cells, and tenocytes produce a wide array of pro-inflammatory mediators. Among these is $PGE_2$, which is known to play a regulatory role by inducing the production of other mediators including cytokines, nitric oxide, and connective tissue degrading metalloproteinase ("MMP") enzymes. Due to its ability to induce MMPs, $PGE_2$ contributes to the breakdown of cartilage ECM. In addition, $PGE_2$ promotes bone resorption and osteophyte formation. $PGE_2$ sensitizes nociceptors on peripheral nerve endings, thereby contributing to the development of inflammatory pain. $PGE_2$ levels are locally regulated by the inducible cyclooxygenase-2 ("COX-2") enzyme, a nitric oxide synthase in chondrocytes that inhibits cartilage and proteoglycan degradation. In pathologic conditions such as osteoarthritis, COX-2 expression is up-regulated with a concomitant increase in $PGE_2$ production.

IL-1β is a proinflammatory cytokine consisting of 153 amino acids with a molecular weight of 17.5 kDa. IL-1β is a member of the interleukin-1 ("IL-1") family and can be produced from a wide variety of cells including, but not limited to, monocytes, macrophages, and dendritic cells as well as B lymphocytes, neutrophils, and natural killer cells after stimulation with microbial ligands acting through toll-like receptors, complement components, other cytokines (such as TNF) or IL-1 itself. Some of the important biological actions of IL-1β include stimulating maturation of T cells, enhancing proliferation of B cells, and promoting expression of inflammatory molecules, including, but not limited to, COX-2, type 2 phospholipase A, $PGE_2$, platelet activating factor and nitric oxide, among others. In some instances, abnormality in production of IL-1β could lead to various kinds of diseases, including, but not limited to, carcinogenesis, autoinflammatory diseases, cryopyrin-associated periodic syndrome ("CAPS"), systemic onset juvenile idiopathic arthritis, and refractory gout. Suppression and regulation of IL-1β can be achieved using various pharmaceutical drugs, however, prolonged administration of these drugs can have adverse side effects. While IL-1β plays a central role in the essential immune response to injury, infection, or inflammation, the deleterious effects that it triggers when dysregulated make IL-1β a target for development of management products for infectious or inflammatory conditions.

The role of other tissues in the inflammation process is also well established. Inflammation of the synovial membrane is now recognized to be a key event in cartilage degradation in osteoarthritis, particularly during the early stages of the disease. Synovitis is characterized by activation of resident macrophage-like cells and fibroblast-like cells in the synovial membrane which leads to production of excessive amounts of pro-inflammatory mediators including TNF-α, IL-1β and PGE$_2$. Recent evidence suggests that synovial macrophages are the main source of the cytokines in the earliest stages of osteoarthritis and that they are important contributors to the cartilage damage in osteoarthritis throughout the course of the disease. Cytokines also induce production of PGE$_2$ and active MMPs. It is now well accepted that these mediators control the balance between ECM destruction and repair, which has made these molecules preferred targets for therapeutic intervention. Other tissues in the joint such as the subchondral bone also produce pro-inflammatory mediators that modulate joint health.

In addition to pro-inflammatory mediators such as cytokines and prostaglandins, reactive oxygen species ("ROS") have also been implicated in joint degeneration observed in osteoarthritis. Oxidative stress induced by ROS, such as nitric oxide and hydrogen peroxide, has been shown to cause chondrocyte apoptosis and cartilage ECM breakdown. Moreover, ROS have been reported to activate signal transduction pathways that lead to an increased production of pro-inflammatory mediators including cytokines and prostaglandins. Studies in vitro have demonstrated a linkage between the pathways involved in the production of ROS and pro-inflammatory mediators. These studies support the notion that agents capable of inhibiting both oxidative stress and inflammation pathways would be particularly useful in the modulation of inflammation.

The central role of COX-2 and PGE2 in the pathophysiology of osteoarthritis is reflected in the widespread use of selective COX-2 inhibitors and a variety of non-selective non-steroidal anti-inflammatory drugs ("NSAIDs") for the treatment of the disorder. However, prolonged administration of these drugs has adverse side effects, including gastrointestinal pathologies and disruption of cartilage proteoglycan metabolism. Studies in human and animal models have demonstrated impaired bone healing and repair with the use of COX inhibitors. Therefore, there is a need for alternative treatments for the management of inflammation that do not center on the use of NSAIDs to inhibit the production of PGE2 and other pro-inflammatory mediators.

Cannabis is a genus of flowering plants in the family Cannabaceae. Plants in this family contain compounds known as cannabinoids, such as Δ$^9$-tetrahydrocannabinol ("THC"), cannabidiol ("CBD"), cannabichromene ("CBC"), cannabigerol ("CBG"), and cannabidivarin ("CBDV"). While THC is known for its psychoactive characteristics, other cannabinoids such as CBD and CBC are not psychoactive. It should be appreciated that the word "cannabinoids" is used in this disclosure to mean any compound that interacts with a cannabinoid receptor and other cannabinoid mimetics.

Cannabinoids have been shown to, among other things, help ameliorate pain and various inflammatory conditions. Cannabinoids, such as THC and CBD, have been found to decrease the production and release of proinflammatory cytokines, including IL-1β, IL-6, and interferon β, from lipopolysaccharide ("LPS") activated cells. CBD, in particular, accomplishes this in a number of ways, including, but not limited to: reducing the activity of the Nuclear factor-kappa B ("NF-κB") pathway (a primary pathway regulating the expression of proinflammatory genes); upregulating the activation of the STAT3 transcription factor (an element of homeostatic mechanisms inducing anti-inflammatory events); decreasing levels of mRNA for the Socs3 gene (a main negative regulator of STATs and particularly of STAT3); and decreasing activation of the LPS-induced STAT1 transcription factor (a key player in interferon β-dependent proinflammatory processes).

ASU has been used to treat osteoarthritis and other forms of arthritis, as well as soft tissue inflammatory conditions. Clinical studies have reported beneficial effects of ASU in human and equine osteoarthritis patients as well as in experimental animal models of osteoarthritis. The mechanisms that could account for some of the beneficial effects of ASU for osteoarthritis have been studied in vitro using bovine and human joint tissue cells. These studies showed that ASU inhibits the expression and production of cytokines, chemokines, PGE$_2$, nitric oxide, and MMPs. ASU also exerts anabolic effects on cartilage metabolism by enhancing synthesis of cartilage matrix components while suppressing their degradation. The mechanism of action of this compound is thought to stimulate chondrocyte expression of transforming growth factor ("TGF") beta 1, TGF beta 2 and plasminogen activator inhibitor 1 ("PAI-1"). By increasing PAI-1, ASU blocks the cascade that leads to MMP activation. ASU also reduces the spontaneous production of stromelysins, IL-6, IL-8 and PGE$_2$ by chondrocytes. Additionally, ASU decreases the effects of IL-1, and thereby reduces chondrocyte and synoviocyte production of collagenase. ASU has also been found to reduce TNF-α, IL-1β, COX-2, and inducible nitric oxide synthase (iNOS) expression in LPS-activated chondrocytes.

Earlier studies using human osteoarthritic chondrocyte cultures found that ASU significantly reduces the stimulating effect of IL-1β on PGE$_2$ production. Of the two isoforms of cyclooxygenases involved in prostaglandin synthesis, COX-2 is highly inducible in response to cytokine exposure. High levels of COX-2 expression have been demonstrated in human synovial tissue. Several studies in experimental animals and humans have shown that PGE$_2$ synthesis and COX-2 expression are upregulated in synovial membranes in osteoarthritis. Increased levels of PGE$_2$ have been detected in synovial tissue and in synovial fibroblasts in osteoarthritis. There is experimental evidence that synovial tissue is the major source of eicosanoids found in osteoarthritic synovial fluid. Cytokines IL-1β and TNF-α enhance synoviocyte production of PGE$_2$. The reported decrease in PGE$_2$ synthesis by ASU appears to be associated with a decrease in COX-2 gene expression.

Although cannabis and ASU have been investigated individually, the effects of combining cannabis and ASU to maintain health and to promote healing have not been examined.

SUMMARY

The present disclosure relates to compositions of cannabis and ASU. In accordance with the purposes and benefits described herein, one contemplated embodiment of the present disclosure relates to novel compositions comprising combinations of cannabis and ASU that exhibit synergistic properties and effectiveness for reduction of inflammatory responses and inflammation in humans and animals. In another contemplated embodiment, the present disclosure relates to novel compositions comprising combinations of ASU and cannabis extract. In yet another contemplated embodiment, the present disclosure relates to novel compositions of certain concentrations of ASU and cannabis oil extract. In still another contemplated embodiment, the present disclosure relates to novel compositions comprising certain concentrations of ASU and cannabis oil extract comprising CBD. In still other contemplated embodiments, the present disclosure relates to novel compositions comprising certain concentrations of ASU and CBD that exhibit synergistic properties and effectiveness for reduction of inflammatory responses and inflammation in humans and animals.

While applicants have recognized a variety of active ingredients ("actives") that tend to exhibit anti-inflammatory properties, it is generally difficult, if not impossible, to predict combinations of such actives that will exhibit synergistic properties and effectiveness for the reduction of inflammatory responses and inflammation. In addition, applicants have recognized that in certain uses it may be desirable to reduce concentrations of actives provided in compositions from a cost perspective or for purposes of reducing possible side effects. However, many actives tend to exhibit relatively little or no effectiveness for the reduction of inflammatory responses and inflammation in humans and animals when provided at reduced concentrations. Thus, the surprising synergy that the applicants have discovered between certain compounds of the compositions described herein also enables the use of lower doses of each compound while achieving relative or greater efficacy for the reduction of inflammatory responses and inflammation in humans and animals. This is beneficial because although these compounds are quite safe, there may be a potential for side effects. In addition, these compounds are costly; for these reasons, the ability to minimize the dose and still achieve beneficial effects is desirable for both safe and cost-effective administration, while achieving relative or greater efficacy for the reduction of inflammatory responses and inflammation in humans and animals.

DETAILED DESCRIPTION

Figure 1:
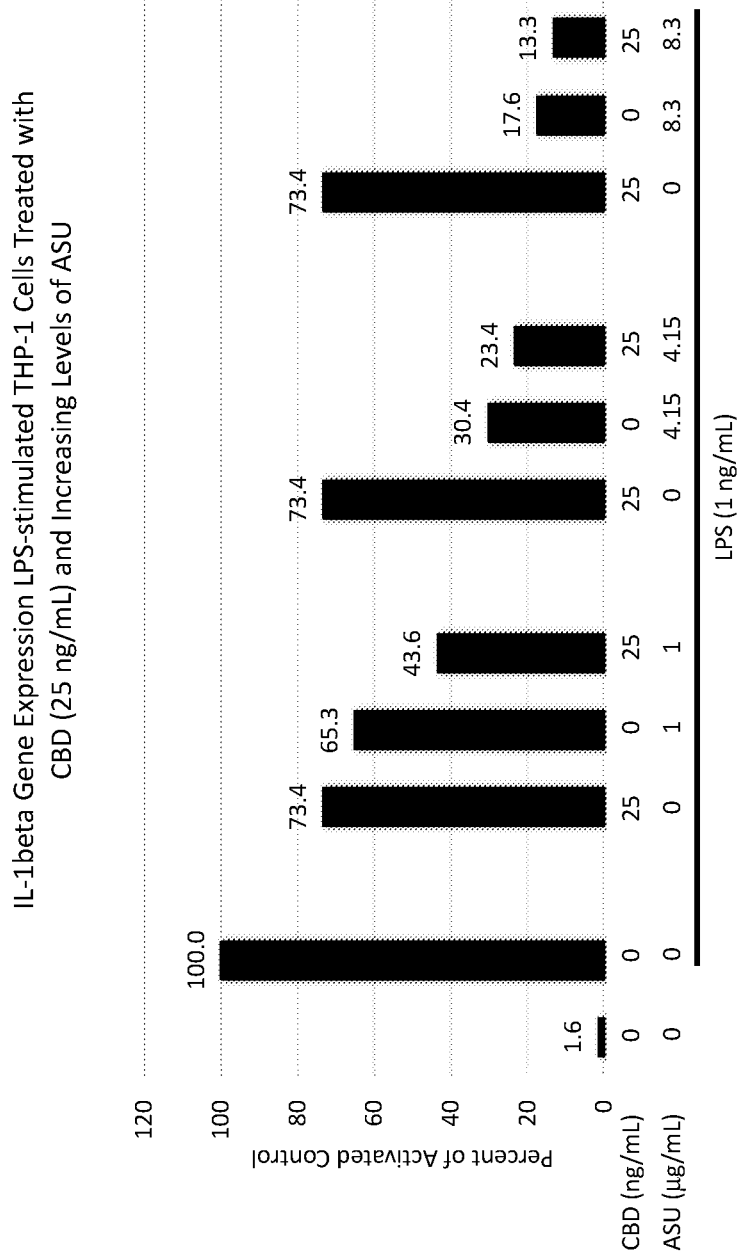
FIG. 1 is a graph showing the effect on IL-1β expression in LPS-stimulated cells exposed to certain concentrations of ASU and *cannabis* oil extract comprising CBD (both individually and in combination) in the experiment described in Example 1.

According to certain contemplated embodiments, the present disclosure relates to novel compositions comprising *cannabis* and ASU. In one contemplated embodiment, the present disclosure relates to novel compositions comprising combinations of *cannabis* and ASU that exhibit synergistic properties. In another embodiment, the present disclosure relates to novel compositions of *cannabis* extract and ASU. In yet another contemplated embodiment, the present disclosure relates to novel compositions comprising *cannabis* oil extract and ASU. In still other contemplated embodiments, the present disclosure relates to novel compositions comprising ASU and *cannabis* oil extract comprising CBD. In still other contemplated embodiments, the present disclosure relates to novel synergistically effective compositions comprising CBD and substantially pure ASU.

*Cannabis* as used in this disclosure can include any component of plants in the Cannabaceae family, such as, for example, the leaves, fruits, seeds, flowers, roots, and stalk of the plants, along with any extracts, isolates, synthetics, powders, oils, or other derivatives thereof and therefrom. This disclosure includes, moreover, compositions which contain mixtures or combinations of *cannabis* plant components along with any extracts, isolates, synthetics, powders, oils, or respective derivatives thereof and therefrom. For example, the *cannabis* leaves, fruits, seeds, roots, flowers, and/or stalks can be air dried, freeze dried, drum dried, spray dried, heat dried and/or partial vacuum dried in a hygienic area and then ground into a powder, including in a cold commercial grinding process. This cold commercial process protects the plant's antioxidant, analgesic, and anti-inflammatory properties from oxygen, light, and heat by cryogenically milling the plant materials. Extracts from the leaf, fruit, seed, root, flower, and/or stalk can be prepared using any conventional extraction methods, including any suitable solvent and/or temperature regime. The *cannabis* plant components can also be harvested from the plant when they are mature and the oil can be removed through conventional practices, including commercial squeezing or extraction methods that avoid heat, light and oxygen to prevent damaging the vitamins, minerals, antioxidants and other active ingredients found in the plant solids, including cold press extraction methods. The present invention can also utilize the cake of the *cannabis* species, which is the byproduct of the process of pressing in order to extract the oil. This process keeps the vitamins, minerals and other active ingredients chemically undamaged during processing. The *cannabis* plant components as described above can then be further processed through mixing. *Cannabis* plant components and combinations and mixtures thereof described above are all intended to be included within the present invention. Thus, in some embodiments, the composition and/or method of the present invention comprises a use of one *cannabis* plant component. In some embodiments, the composition and/or method of the present invention comprises a use of one or more *cannabis* plant components. In some embodiments, the composition and/or method of the present invention comprises a use of a powder, an extract, an oil, or a seed cake, or a mixture or combination thereof.

*Cannabis* oil extract as used in this disclosure can include any and all oil extracts from any plant in the family Cannabaceae, or any mixtures or combinations thereof. Such oil extract may be further combined with any components, extracts, isolates, powders, oils, synthetics, or other derivatives from *cannabis* plants and further contemplates any mixtures or compounds or combinations thereof. In one contemplated embodiment, the *cannabis* oil extract comprises CBD, and may be extracted from non-psychoactive hemp (also known as industrial hemp), which contains a THC concentration of no more than 0.3% on a dry-weight basis. The disclosure contemplates, however, *cannabis* oil extract comprising CBD from any *cannabis* plant, and may, for example, include greater than 0.3% THC on a dry-weight basis or be extracted from psychoactive marijuana or any plant in the family Cannabaceae. In yet another contemplated embodiment, a *cannabis* oil extract comprising CBD further comprises a full spectrum of all compound classes obtained from the *cannabis* plants. In yet another contemplated embodiment, a *cannabis* oil extract comprising CBD further comprises terpenes and flavonoids. In some embodiments of the present invention, a *cannabis* oil extract is a hemp oil and may be a commercially available preparation, such as NMXCB1220™ from Travco Products, Inc., Lancaster, S.C.

In still other contemplated embodiments, CBD may be sourced from any plant in the family Cannabaceae or synthesized from other sources. In still other contemplated embodiments, pure or substantially pure CBD may be administered. CBD (CAS No. 13956-29-1) has a molecular formula of $C_{21}H_{30}O_2$ and the IUPAC nomenclature of 2-[(1R,6R)-3-methyl-6-prop-1-en-2-ylcyclohex-2-en-1-yl]-5-pentylbenzene-1,3-diol, and may be sourced from a number of commercial suppliers. The compounds and combinations thereof described above are all intended to be included within the present disclosure.

A single-dose pharmacokinetic study of CBD was carried out by Gamble, et al. (Gamble, L. J., J. M. Boesch, C. W. Frye, W. S. Schwark, S. Mann, L. Wolfe, H. Brown, E. S. Berthelsen, and J. J. Wakshlag. 2018. "Pharmacokinetics, Safety, and Clinical Efficacy of Cannabidiol Treatment in Osteoarthritic Dogs", *Front Vet Sci,* 5: 165) in which beagle dogs were orally administered either 2 mg/kg or 8 mg/kg CBD in olive oil. The median maximal concentration of CBD in serum was 102.3 ng/mL for the 2 mg/kg dose and 590.8 ng/mL for the 8 mg/kg dose. In addition, four single-dose pharmacokinetic studies were carried out to assess the plasma levels of CBD using a wide range of CBD levels in humans. Agurell et al. (Agurell, S., S. Carlsson, J. E. Lindgren, A. Ohlsson, H. Gillespie and L. Hollister. 1981. "Interactions of delta 1-tetrahydrocannabinol with cannabinol and cannabidiol following oral administration in man. Assay of cannabinol and cannabidiol by mass fragmentography", *Experientia,* 37(10): 1090-2) observed a mean plasma level of 5.5 ng/mL CBD after oral administration of 40 mg of CBD. Guy et al. (Guy, G. W., and P. Robson. 2004. "A Phase I, Open Label, Four-Way Crossover Study to Compare the Pharmacokinetic Profiles of a Single Dose of 20 mg of a *Cannabis* Based Medicine Extract (CBME) Administered on 3 Different Areas of the Buccal Mucosa and to Investigate the Pharmacokinetics of CBME per Oral in Healthy Male and Female Volunteers", *Journal of Cannabis Therapeutics,* 3(4): 79-120) detected a $C_{MAX}$ of 2.47 ng/mL following a 10 mg dose of CBD. Nadulski et al. (Nadulski, T., F. Sporkert, M. Schnelle, A. M. Stadelmann, P. Roser, T. Schefter and F. Pragst. 2005. "Simultaneous and sensitive analysis of THC, 11-OH-THC, THC-COOH, CBD, and CBN by GC-MS in plasma after oral application of small doses of THC and *cannabis* extract", *J Anal Toxicol,* 29(8): 782-9) reported a mean plasma concentration of 0.95 ng/mL CBD 1 h after oral intake of 5.4 mg dose. Taylor et al. (Taylor, L., B. Gidal, G. Blakey, B. Tayo and G. Morrison. 2018. "A Phase I, Randomized, Double-Blind, Placebo-Controlled, Single Ascending Dose, Multiple Dose, and Food Effect Trial of the Safety, Tolerability and Pharmacokinetics of Highly Purified Cannabidiol in Healthy Subjects", *CNS Drugs,* 32(11): 1053-67) studied the highly purified oral CBD solution, Epidolex®, and determined that 1500, 3000, 4500 and 6000 mg resulted in peak plasma levels of 292.4, 533, 722.1 and 782 ng/mL, respectively.

Dosage calculations can be determined by those of skilled in the art by evaluating body weight, surface area, and species differences. Similarly, dosages for cross-species extrapolation can be calculated by one skilled in the art using conventional dose conversion methods.

The dosage rate of CBD may be from about 0.001 mg/kg to about 100 mg/kg.

According to some exemplary embodiments, CBD may be administered at a dose of about 2.8 to about 66.5 mg per kg bodyweight of a human subject (i.e. about 169 to about 3992 mg for a 60 kg human subject).

According to some exemplary embodiments, CBD may be administered at a dose of about 1.05 to about 8 mg per kg bodyweight of a dog subject (i.e. about 10.5 to about 80 mg for a 10 kg dog subject).

ASU as used in this disclosure can include any or all avocado/soybean extracts or mixtures or combinations of such extracts which contain any or all unsaponifiable lipids and/or combinations thereof. "Unsaponifiables" are compounds which do not react with alkali to form a soap. The term "avocado unsaponifiables" refers to an extract of compounds obtained from any part of an avocado (genus *Persea*). The avocado may be any species of avocado, such as but not limited to *Persea americana* and *Persea schiedeana*. The term "soybean unsaponifiables" refers to an extract of compounds obtained from any part of a soybean (*Glycine max*). The soybean may be any species of soybean, such as but not limited to *Glycine willd*. Avocado/soybean unsaponifiables are well known in the art and are described in numerous patents and publications, including but not limited to: U.S. Pat. Nos. 6,797,289, 6,759,543, 7,449,487, 8,568,803, 8,808,770, 8,846,118, 9,572,791, 10,456, 372, and 10,485,784; U.S. Patent Application Publication No. 20080176935; "Unsaponifiable constituents of avocado and soya oils. Treatment of certain forms of arthralgia," *J. Med. Lyon* 53 (222): 195-8 (February 1972); Trevoux, "Unsaponifiable fractions of the avocado and soybean in gynecology," *J. Gynecol. Obstet. Biol. Reprod.* 6 (1): 99-105 (January 1977); Lamaud et al., "Biochemical modifications of connective tissue induced by the non-saponifiables of avocado and soy-bean oils administered percutaneously in the hairless rat," *Pathol. Biol.* 26 (5): 269-74 (May-June 1978); Boumediene et al., "Avocado/soya unsaponifiables enhance the expression of transforming growth factor beta 1 and beta 2 in cultured articular chondrocytes," *Arthritis Rheum.* 42 (1): 148-56 (January 1999); Henrotin et al., "Effects of three avocado/soybean unsaponifiable mixtures on metalloproteinases, cytokines and prostaglandin E2 production by human articular chondrocytes," *Clin. Rheumatol.* 17 (1): 31-9 (1998); Maheu et al. "Symptomatic efficacy of avocado/soybean unsaponifiables in the treatment of osteoarthritis," *Arthritis Rheum.* 41 (1): 81-91 (January 1998); and Blotman et al., "Efficacy and safety of avocado/soybean unsaponifiables in the treatment of symptomatic osteoarthritis," *Rev. Rheum. Engl. Ed.* 64 (12): 825-34 (December 1997), which are each incorporated by reference herein in their entirety. In addition, avocado/soybean unsaponifiables in combination with another ingredient (glucosamine) are currently marketed in the United States under the trade name COSAMIN® ASU. Avocado/soybean unsaponifiables are also marketed in Europe under the trade name PIASCLEDINE®. In one contemplated embodiment, the ASU may be NMX1000® available from Nutramax Laboratories, Inc. The disclosure includes, moreover, compositions which contain avocado unsaponifiables, soy unsaponifiables, or mixtures or combinations of such avocado unsaponifiables and soy unsaponifiables. The compounds and combinations thereof described above are all intended to be included within the present disclosure.

Dosage calculations can be determined by those of skilled in the art by evaluating body weight, surface area, and species differences. Similarly, dosages for cross-species extrapolation can be calculated by one skilled in the art using conventional dose conversion methods.

The dosage rate of ASU may be from about 0.25 mg/kg to about 12 mg/kg.

According to some exemplary embodiments, ASU may be administered at a dose of about 0.41 to about 8.3 mg per kg bodyweight of a human subject (i.e. about 25 to about 500 mg for a 60 kg human subject).

According to some exemplary embodiments, ASU may be administered at a dose of about 0.25 to about 8.3 mg per kg bodyweight of a dog subject (i.e. about 2.5 to about 83 mg for a 10 kg dog subject).

EXAMPLES

Example 1

Figure 2:
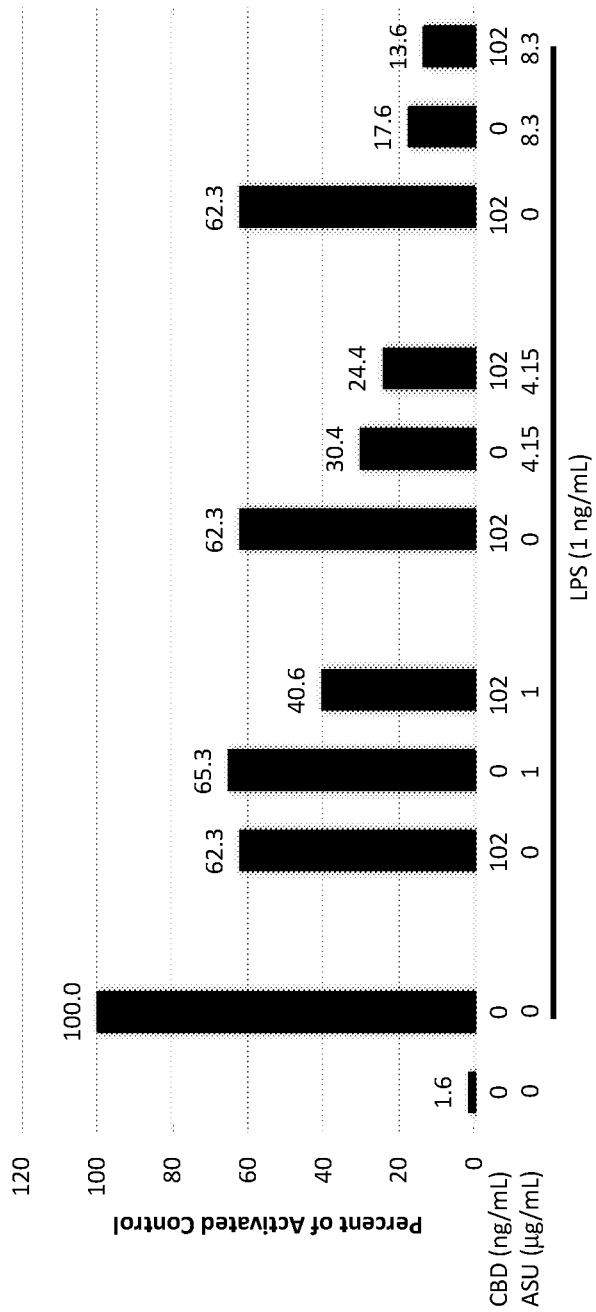
FIG. 2 is a graph showing the effect on IL-1β expression in LPS-stimulated cells exposed to certain concentrations of ASU and *cannabis* oil extract comprising CBD (both individually and in combination) in the experiment described in Example 1.
Figure 3:
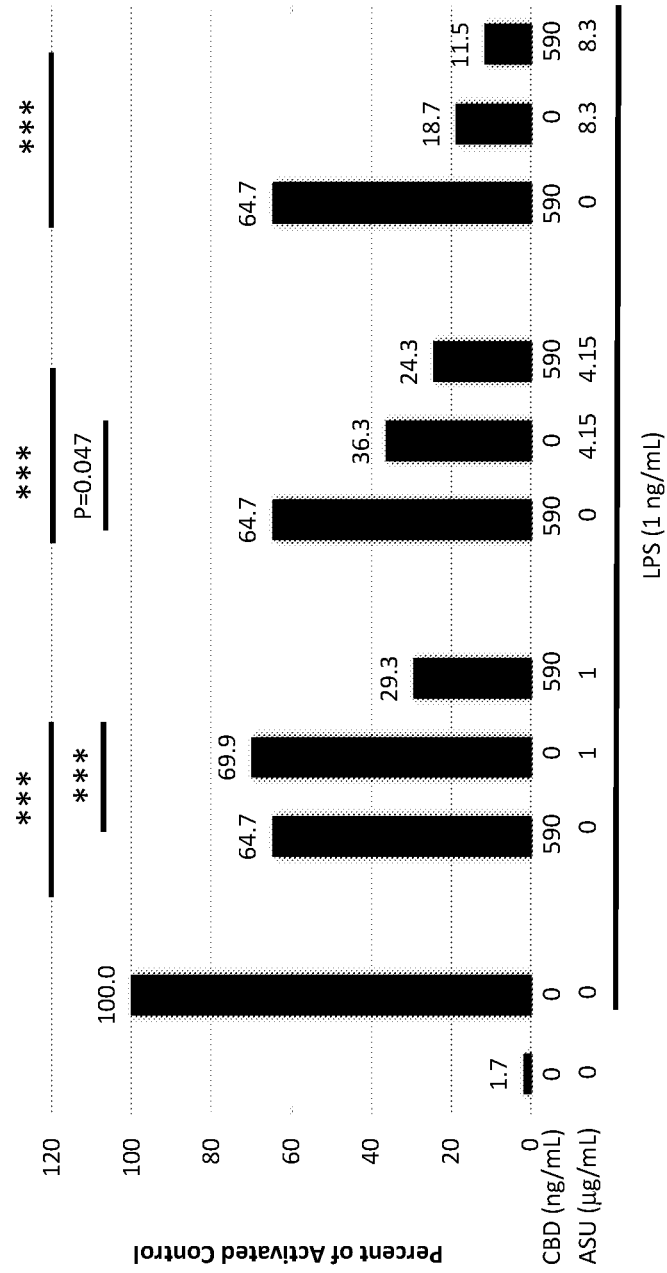
FIG. 3 is a graph showing the effect on IL-1β expression in LPS-stimulated cells exposed to certain concentrations of ASU and *cannabis* oil extract comprising CBD (both individually and in combination) in the experiment described in Example 1.

FIGS. 1-3 illustrate the effect of ASU and cannabidiol CBD on IL-1β gene expression in LPS-stimulated THP-1 human monocyte/macrophage cells in a first experiment.

THP-1 human monocyte/macrophage cells were co-treated with 1 ng/mL LPS and with 25, 102 or 590 ng/mL CBD alone, 1, 4.15 or 8.3 µg/mL ASU alone, or each of the three concentrations of ASU combined with each of the three concentrations of CBD for 24 hours. LPS is an endotoxin in the bacterial cell wall capable of inducing an inflammatory response which includes an increased expression of IL-1β. Cells were harvested for RNA isolation and processed for quantitative RT-PCR analysis to assess IL-1β gene expression. Statistical comparisons were made using one-way analysis of variance ("ANOVA") with Holm-Sidak's method for multiple group comparisons. Differences of $P<0.05$ were considered significant.

In all combinations examined, the suppression of IL-1β was greater than the individual ingredients alone. Statistically significant reductions in the expression of IL-1β were observed in cells treated with the combination of 590 ng/mL CBD with either 1 or 4.15 µg/mL ASU compared to either ASU ($P<0.001$) or CBD ($P<0.001$) alone (see FIG. 3).

Example 2

Figure 4:
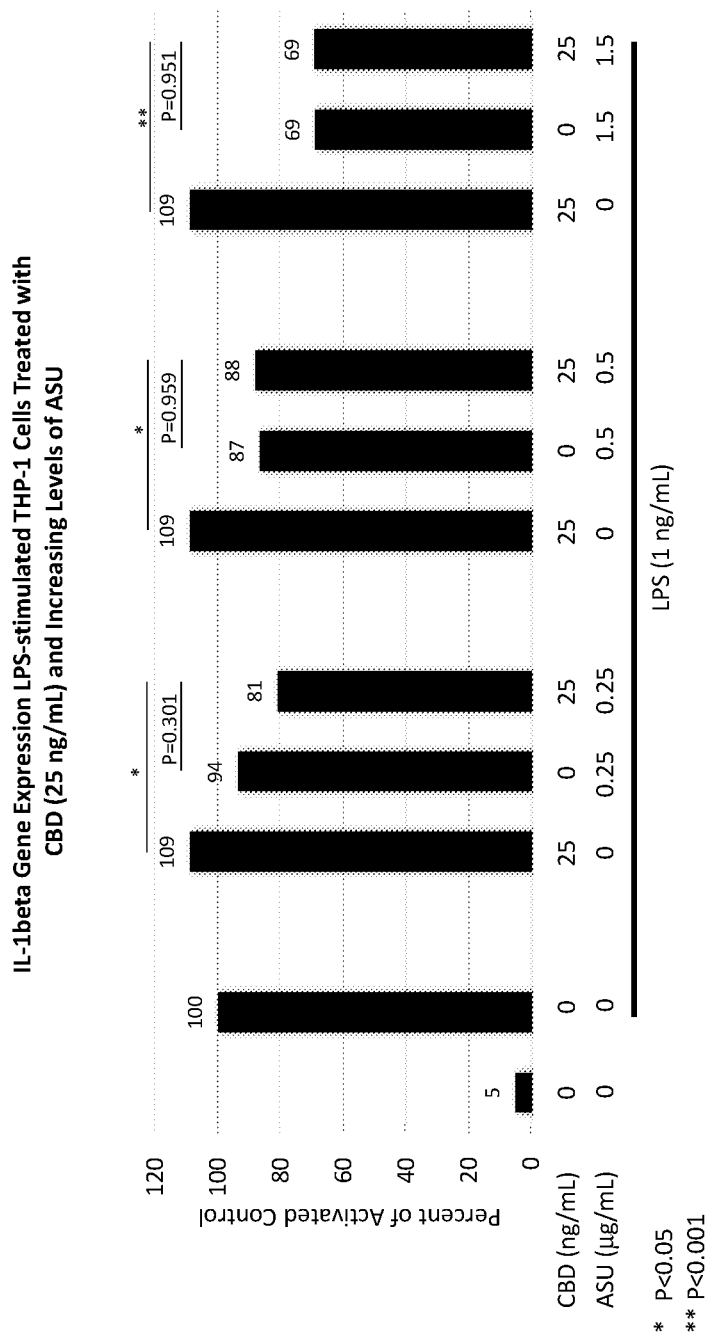
FIG. 4 is a graph showing the effect on IL-1β expression in LPS-stimulated cells exposed to certain concentrations of ASU and *cannabis* oil extract comprising CBD (both individually and in combination) in the experiment described in Example 2.
Figure 5:
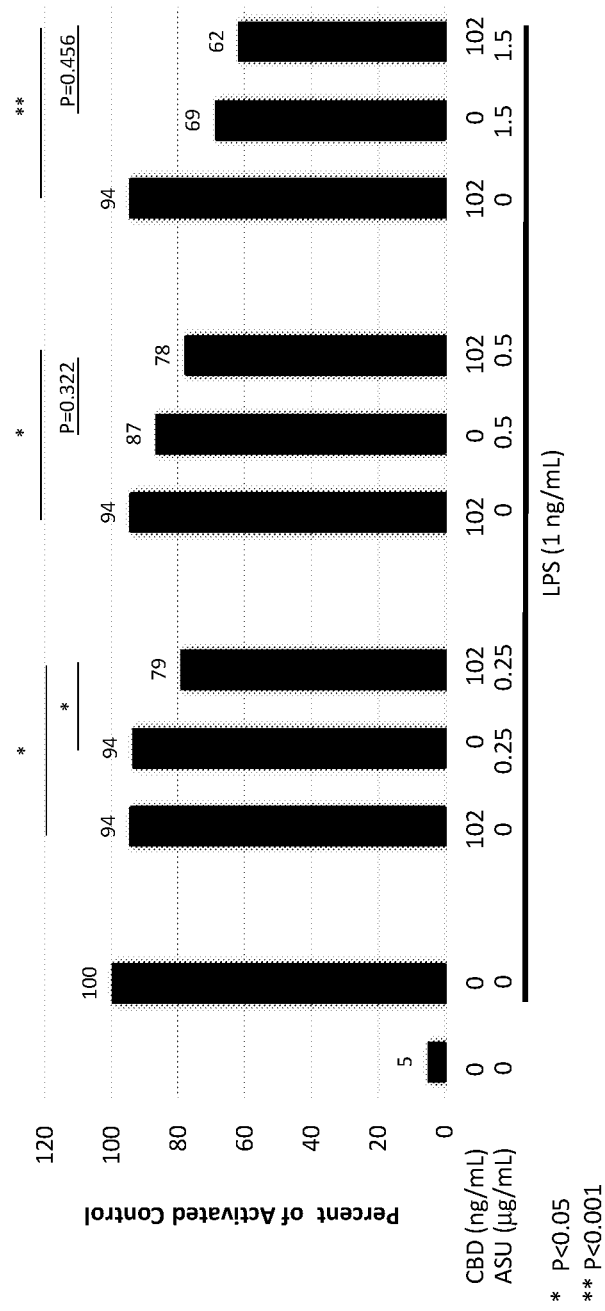
FIG. 5 is a graph showing the effect on IL-1β expression in LPS-stimulated cells exposed to certain concentrations of ASU and *cannabis* oil extract comprising CBD (both individually and in combination) in the experiment described in Example 2.
Figure 6:
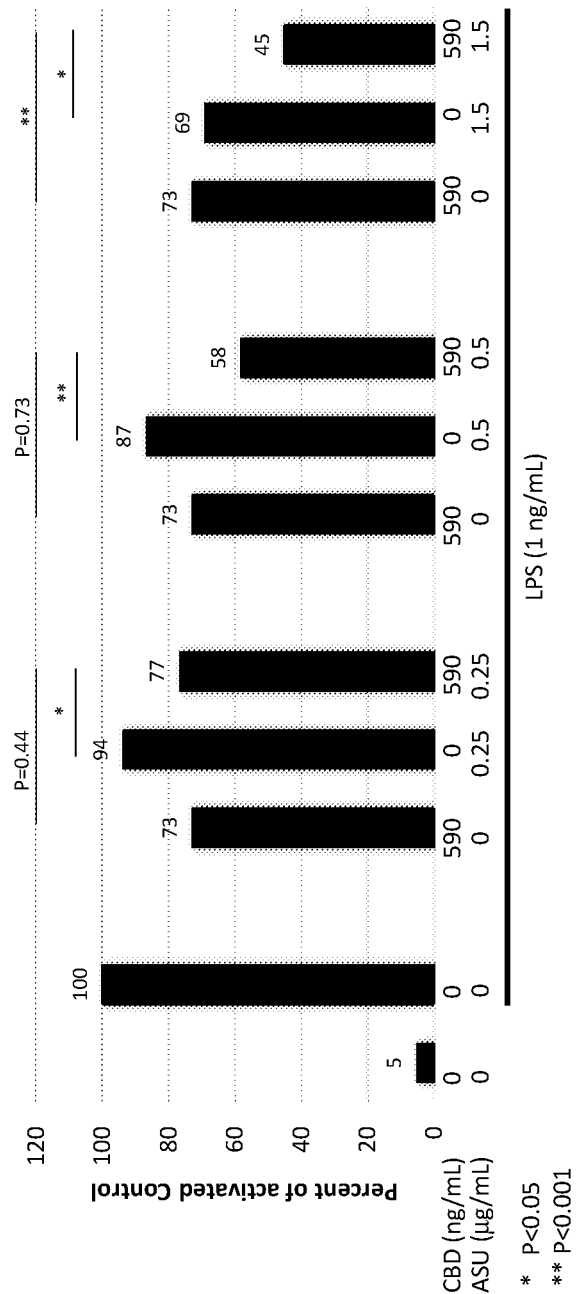
FIG. 6 is a graph showing the effect on IL-1β expression in LPS-stimulated cells exposed to certain concentrations of ASU and *cannabis* oil extract comprising CBD (both individually and in combination) in the experiment described in Example 2.

FIGS. 4-6 illustrate the effect of ASU and cannabidiol CBD on IL-1β gene expression in LPS-stimulated THP-1 human monocyte/macrophage cells in a second experiment.

THP-1 human monocyte/macrophage cells were co-treated with 1 ng/mL LPS and with 25, 102 or 590 ng/mL CBD alone, 0.25, 0.5 or 1.5 µg/mL ASU alone, or each of the three concentrations of ASU combined with each of the three concentrations of CBD for 24 hours. Cells were harvested for RNA isolation and processed for quantitative RT-PCR analysis to assess IL-1β gene expression. Statistical comparisons were made using one-way ANOVA with Holm-Sidak's method for multiple group comparisons. Differences of $P<0.05$ were considered significant.

In several combinations examined, the suppression of IL-1β was greater than the individual ingredients alone. Statistically significant reductions in the expression of IL-1β were observed in cells treated with the combination of 102 ng/mL CBD with 0.25 µg/mL ASU compared to either ASU ($P<0.001$) or CBD ($P<0.001$) alone (see FIG. 5).

As such, the combination of various concentrations of ASU and CBD exhibit unexpected synergistic properties and effectiveness for reduction of inflammatory responses. Synergy refers to the effect wherein a combination of two or more components provides a result which is greater than the sum of the effects produced by the agents when used alone. In certain embodiments, the result is statistically significant and greater than the additive effect.

In still other embodiments, the ASU and *cannabis* composition may be contained in acceptable excipients and/or carriers for appropriate formulation. The carrier may be a liquid, gel, gelcap, capsule, powder, solid tablet (coated or non-coated), tea, or the like. Suitable excipient and/or carriers include vegetable oil, fish oil, hill oil, maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). The various ingredients and the excipient and/or carrier may be mixed and formed into the desired form using conventional techniques.

In one aspect, the present disclosure provides methods of preventing and/or reducing an inflammatory response and/or inflammation in a subject. In one aspect, the present disclosure provides methods for managing inflammatory disorders or generally reducing inflammatory burden of a human or non-human animal. Accordingly, in one embodiment the present disclosure provides a method of preventing and/or reducing an inflammatory response and/or inflammation in one or more tissues, the method including delivering to the one or more tissues the compositions of the present disclosure.

In certain embodiments, the compositions of this disclosure can be used in methods for treating, preventing, regulating, or managing inflammatory disorder selected from the comprising increased blood levels of C-reactive protein, systemic lupus erythematosis, Reye's syndrome, rheumatic fever, allergic rhinitis, myasthenia gravis, temporal arteritis, vasculitis, inflammatory diseases of the skin including psoriasis, atopic dermatitis, rosacea, eczema, alopecia universalis, scleroderma, pemphigus, contact dermatitis, ankylosing spondylitis, dermatomyositis, polymyositis, celiac sprue, Guillain-Barré syndrome, multi-infarct dementia, post-cerebral vascular accident reperfusion damage, Addison's disease, Hashimoto's thyroiditis, asthma, upper respiratory inflammation symptoms, chronic bronchitis, atherosclerosis, pernicious anemia, autoimmune hepatitis, prostatitis, pelvic inflammatory disease, Goodpasture's syndrome, Wegener's granulomatosis, Sjogren's syndrome, or allergic conjunctivitis, inflammatory diseases of the eye including corneal dystrophy, trachoma, onchocerciasis, uveitis, sympathetic ophthalmitis and endophthalmitis, inflammatory bowel diseases such as ileitis, ulcerative colitis, Barrett's syndrome, and Crohn's disease, chronic inflammatory diseases of the gum, including gingivitis and periodontitis; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, Epilepsy, amyotrophic lateral sclerosis and viral or autoimmune encephalitis, preeclampsia; chronic liver failure.

In another aspect, the present disclosure provides methods for managing joint health or joint disease/disorder (e.g., arthritis). In certain embodiments, the compositions of this disclosure can be used in methods for treating, preventing, supporting, maintaining, or managing joint cartilage, minimizing cartilage degradation, promoting healthy joints by protecting cartilage integrity, diminishing the action of enzymes that affect joint health, improving joint movement and/or function, alleviating joint pain, alleviating joint stiffness, improving joint range of motion and/or flexibility, promote mobility, and/or any combination thereof.

One will appreciate that the novel combinations of the present disclosure can be administered in any amount, including but not limited to a physiologically effective or acceptable dosage. As used herein, "a physiologically effective dosage" may include an amount which is administered under any defined dosing regimen for either clinical, pharmaceutical, medicinal, veterinary, dietary or nutritional purposes. Thus a "physiologically effective dosage" or a "physiologically acceptable dosage" may include a therapeutically effective dosage, a pharmaceutically acceptable dosage, a veterinary acceptable dosage, a nutraceutically acceptable dosage, a dietary acceptable dosage and a nutritionally acceptable dosage, all of which are included for use in the present disclosure.

The novel combinations of the present disclosure can be administered or combined in any manner and presented to the human or non-human animal in any form, alone or in combination. In one embodiment, the composition comprises a unit dosage form, including but not limited to pharmaceutical dosage forms suitable for oral, rectal, intravenous, subcutaneous, intramuscular, transdermal, transmucosal, and topical. In one embodiment, the composition comprises an orally administrable dosage form. Examples of orally administrable dosage forms include, but are not limited to a tablet, capsule, powder that can be dispersed in a liquid or sprinkled on food, a liquid such as a solution, suspension, or emulsion, a soft gel/chew capsule, a chewable bar, or other convenient dosage form known in the art. In some embodiments, the composition comprises a tablet, capsule, or soft chewable treat. The orally administrable dosage forms may be formulated for immediate release, extended release or delayed release. The composition may be coated or uncoated.

The compounds of the present disclosure have several advantages over conventional therapies for connective tissue disorders in human and non-human subjects, such as excellent safety profiles. This is in part related to the fact that these compounds occur normally in the body or in various foods. Another characteristic shared by the compounds is tendency for a slow onset of action. Pharmaceuticals, such as NSAIDs, tend to cause sudden changes in the symptoms of disease. The endogenous compounds in the present disclosure work more slowly, by normalizing structures and functions within the body.

Some embodiments of the present disclosure relate to combinations and therapeutic administration of the combinations of the present disclosure with one or more active ingredients that are commonly prescribed or used for treatment of and/or prophylaxis of a joint or inflammatory disease/disorder in a subject including, but not limited to, analgesics, NSAIDs, disease-modifying antirheumatic drugs ("DMARDs"), corticosteroids, anakinra (an IL-1 receptor antagonist), COX-2 inhibition, gamma-aminobutyric acid-B ("GABAB") receptor agonists, such as baclofen, gamma-aminobutyric acid-A ("GABAA") potentiating drugs, such as the benzodiazepines, TNF-inhibiting drugs, glucosamine, glucosamine salt, chondroitin, chondroitin salt, hyaluronic acid, *Boswellia serrata* extract, acetyl-11-keto-boswellic acid, methylsulfonylmethane, collagen type II, L-ergothionine, resveratrol, and other drugs and/or nutritional supplements.

Some embodiments of the present disclosure relate to combinations and therapeutic administration of the combinations of the present disclosure with one or more active ingredients that are commonly prescribed or used for treatment of and/or prophylaxis of a degenerative disease/disorder in a subject include, but are not limited to, NSAIDs, COX-2 inhibition, GABAB receptor agonists, such as baclofen, and GABAA potentiating drugs, such as the benzodiazepines.

Some embodiments of the present disclosure relate to combinations and therapeutic administration of the combinations of the present disclosure with one or more active ingredients that are commonly prescribed or used for treatment of and/or prophylaxis of a soft tissue disease/disorder in a subject include, but are not limited to, milnacipram, pregabalin, SNRIs, NSRIs, muscle relaxers, sedatives, painkillers, and NSAIDs.

In some embodiments, the novel combinations of the present disclosure may be included in a kit with a separate dosage form containing at least one other active ingredient, exemplified by one or more compounds suitable for the treatment of or commonly prescribed or used for the treating and/or prophylaxis of a joint or inflammatory disease/disorder (e.g. arthritis).

In some embodiments, the novel combinations of the present disclosure may be included in a kit with a separate diagnostic agent or tool exemplified by one or more agents/tools suitable for use as part of a diagnostic test. In certain embodiments the diagnostic agent or tool is used as part of a test for measuring the levels of one or more biomarkers.

The foregoing descriptions of various embodiments of the disclosure are provided for purposes of illustration and are not intended to be exhaustive or limiting. Modifications or variations are also possible in light of the above teachings. The embodiments described above were chosen to provide the best application to thereby enable one of ordinary skill in the art to utilize the disclosed disclosures in various embodiments and with various modifications as are suited to the particular use contemplated. All such modifications and variations are within the scope of the disclosure.

All references cited herein are incorporated by reference in their entirety.

What is claimed:

1. A composition comprising a synergistic combination of avocado/soybean unsaponifiables and cannabinoids.

2. The composition of claim 1, wherein the cannabinoids comprise cannabidiol.

3. The composition of claim 2, wherein the source of the cannabinoids is *cannabis*.

4. The composition of claim 3, wherein the source of the cannabidiol is a *cannabis* extract.

5. The composition of claim 3, wherein the source of the cannabidiol is a *cannabis* oil extract.

6. The composition of claim 2, wherein the cannabidiol is synthetic.

7. The composition of claim 1, further comprising terpenes.

8. The composition of claim 1, further comprising flavonoids.

9. The composition of claim 1, formulated for oral administration to an avian subject.

10. The composition of claim 1, formulated for oral administration to a mammalian subject.

11. The composition of claim 9, wherein the mammalian subject is selected from the group consisting of a human, dog, cat, horse, camel, or cow.

12. A method of reducing levels of one or more inflammatory mediators comprising administering to a subject in need thereof a synergistic combination of avocado/soybean unsaponifiables and cannabinoids.

13. The method of claim 12, wherein the cannabinoids comprise cannabidiol.

14. The method of claim 13, wherein the source of the cannabidiol is *cannabis*.

15. The method of claim 13, wherein the source of the cannabidiol is a *cannabis* extract.

16. The method of claim 13, wherein the source of the cannabidiol is a *cannabis* oil extract.

17. The method of claim 13, wherein the cannabidiol is synthetic.

18. The method of claim 12, wherein the synergistic combination further comprises terpenes.

19. The method of claim 12, wherein the synergistic combination further comprises flavonoids.

20. The method of claim 12, wherein the synergistic combination is formulated for oral administration to an avian subject.

21. The method of claim 12, wherein the one or more inflammatory mediators are selected from the group consisting of interleukin-1$\beta$, interleukin-6, and interferon $\beta$.

22. The method of claim 12, wherein the synergistic combination is formulated for oral administration to a mammalian subject.

23. The method of claim 22, wherein the mammalian subject is selected from the group consisting of a human, dog, cat, horse, camel, or cow.

* * * * *